(12) United States Patent
Johnston, Jr. et al.

(10) Patent No.: US 7,850,665 B2
(45) Date of Patent: Dec. 14, 2010

(54) MULTIPLE FLUID DELIVERY DEVICE FOR POULTRY

(75) Inventors: Joseph H. Johnston, Jr., Gainesville, GA (US); Christopher Davis Leslie, Cleveland, GA (US)

(73) Assignee: Merial Limited, Duluth, GA (US)

( * ) Notice: Subject to any disclaimer, the term of this patent is extended or adjusted under 35 U.S.C. 154(b) by 218 days.

(21) Appl. No.: 11/959,400

(22) Filed: Dec. 18, 2007

(65) Prior Publication Data
US 2008/0177223 A1    Jul. 24, 2008

Related U.S. Application Data

(60) Provisional application No. 60/871,084, filed on Dec. 20, 2006.

(51) Int. Cl.
*A61M 5/32* (2006.01)
(52) U.S. Cl. ...................... 604/272; 604/191
(58) Field of Classification Search ................. 604/68, 604/191, 247, 272
See application file for complete search history.

(56) References Cited

U.S. PATENT DOCUMENTS

| 4,158,035 | A | | 6/1979 | Haase et al. |
| 4,758,227 | A | * | 7/1988 | Lancaster et al. ........... 604/144 |
| 5,176,101 | A | * | 1/1993 | Paul et al. .................... 119/6.8 |
| 5,312,353 | A | | 5/1994 | Boggess et al. |
| 5,468,227 | A | * | 11/1995 | Haskell ...................... 604/156 |
| 6,789,467 | B2 | * | 9/2004 | Johnston et al. ............... 99/532 |
| 6,981,470 | B2 | * | 1/2006 | Gross et al. ................. 119/322 |
| 2007/0083155 | A1 | * | 4/2007 | Muller ........................ 604/91 |

* cited by examiner

*Primary Examiner*—Nicholas D Lucchesi
*Assistant Examiner*—Gerald Landry, II
(74) *Attorney, Agent, or Firm*—Judy Jarecki-Black; Chad Kitchen; Merial Limited

(57) ABSTRACT

The present invention provides an injection delivery system for the injection delivery of at least two fluid doses to a small bird by penetrating the skin of the recipient bird with at least one injection needle. The present injection delivery system comprises an injection needle device and a metering device. The injection needle device can either be a stationary unit or a hand held device.

1 Claim, 10 Drawing Sheets

US 7,850,665 B2

MULTIPLE FLUID DELIVERY DEVICE FOR POULTRY

INCORPORATION BY REFERENCE

This application claims benefit of U.S. provisional patent application Ser. No. 60/871,084 filed Dec. 20, 2006.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a device for the injection delivery of drugs or vaccines to birds. More specifically, the present invention relates to a metered injection device that provides for the simultaneous subcutaneous or intramuscular injection of up to four different doses of drugs or vaccines into bird.

BACKGROUND OF THE INVENTION

Inoculation of one-day old chicks or other small birds using automatic vaccine injection devices is known in the poultry industry. Automatic bird injection devices, including devices suitable for injecting small bird such as one-day chicks, are described, for example, in U.S. Pat. Nos. 5,312,353, 4,863,443, 4,758,227, 4,681,565, 4,515,590, 4,276,879, 4,177,810, 4,108,176, 3,964,481, 3,641,998. Such automated devices can allow one person to inoculate a multitude of birds with the significant economic benefit of reduced labor costs.

These automatic injection devices generally provide a movable reciprocating carrier that supports a single injection needle assembly connected to a fluid supply container. The carrier may be actuated relative to a support surface against which the chick is maintained by the operator. Once the needle reaches its extended position, and when it has penetrated into the tissue of the bird, a syringe or other dose delivery means is actuated to deliver the required dose from the supply container to the recipient bird.

It may also be desirable to separately administer different drugs or vaccines. U.S. Pat. No. 4,758,227, for example, provides two injection needles configured to be simultaneously introduced into the bird's breast muscle tissue. This automatic injection system can inject two doses at the same time. The diminutive size of intended recipient birds, such as one-day chicks, however, has limited available automatic injectors to delivering the separate doses to the breast muscle tissue on opposite sides of the keel bone.

Many therapeutic compositions are not stable or are otherwise incompatible when co-mingled. Such combinations must be injected either consecutively and/or injected into different localities in the recipient bird. Further, for vaccines or drugs that need to be administered subcutaneously into the necks of one-day old chicks, a procedure that requires more precise and limited penetration of the bird than is generally practiced by available automatic injection delivery systems is necessary. Manual injections of the drugs or vaccines are still the only procedure available, with the main drawback of reduced production. Moreover, to inject a second dose of a drug or vaccine, the birds must be rehandled, inducing undue stress in the bird and significant increases in costs.

Commonly assigned U.S. Pat. No. 6,789,467 (the "'467 patent") discloses a system for the injection delivery of at least two fluid doses to a small bird by penetrating the skin of the recipient bird with at least two injection needles. It is possible with the injection delivery system of the '467 patent to simultaneously inject drugs, or other fluid vaccines that do not mix well or whose mixture would be detrimental to the stability or efficacy of the active ingredients therein. Preferably, the injection ends of the injection needles penetrate the skin of the recipient bird concurrently and deliver the fluid doses to a small target tissue area. The injection delivery system provides an injection needle support for connecting the injection needles to dose distributors and fluid supply containers while maintaining the injection ends of the injection needles in a substantially parallel arrangement to allow for penetration of the bird's skin by both needles.

In addition to having a device that can inject multiple doses of vaccines or drugs simultaneously, it is important to have a device that performs this function repeatedly and accurately. Precise metering of fluids such as vaccines and drugs is important where fluids with known compositions must be conveyed at precisely definable rates or in precise quantities or doses. Metering or pumping devices provide for delivering, balancing and metering of fluids. Such metering devices typically include a driving device and a piston unit. Metering devices also typically include a hydraulic unit having a space to accommodate a hydraulic fluid that is connected to the piston of the piston unit.

Thus, there exists a need for an automatic inoculating system for small birds, especially for one-day chicks, that can automatically deliver two or more separate doses of therapeutic fluids such as drugs or vaccines repeatedly and accurately via a subcutaneous route.

Citation or identification of any document in this application is not an admission that such document is available as prior art to the present invention.

SUMMARY OF THE INVENTION

The present invention provides systems for the injection delivery of at least two fluid doses to a bird, whether newly hatched or older, by penetrating the skin of the recipient bird with at least one injection needle. In addition to being able to inject fluids such as vaccines and drug compositions that are compatible and stable when mixed with one another, it is possible with the injection delivery system of the present invention to simultaneously inject drugs, or other fluid vaccines that do not mix well or whose mixture would be detrimental to the stability or efficacy of the active ingredients therein. Preferably, the injection ends of the injection needles will penetrate the skin of the recipient bird concurrently and deliver the fluid doses to a small target tissue area. The present invention provides an injection needle support for connecting the injection needles to a metering device while maintaining the injection ends of the injection needles in a substantially parallel arrangement to allow for penetration of the bird's skin by both needles. When injecting vaccines or drugs that are compatible and can be mixed with one another, a single needle may be used to deliver the vaccines or drugs.

The injection needle support typically is attached to a carrier operably connected to an actuator, an actuator power source and a switch mechanism wherein the actuator, when activated, can reciprocally move the carrier and injection support toward and away from an injection position. The injection delivery system may further include a metering device for delivering multiple fluid doses to the injection needles for injection into a recipient bird held against an aperture in a retaining plate. When the carrier and injection needle support are in an extended position, the injection needles attached project through the apertures of the needle support and penetrate a selected area of the skin of the recipient bird. The fluid dose(s) is then delivered through the injection needles to the bird. The injection needle support of the present invention generally comprises a base, a base plate having recesses for receiving hubs of the injection needles, and an end plate having bores for receiving the shank portions of the injection needles. The needle support further comprises fluid connections for delivering fluid doses to the needles and which communicate with the recesses and the hubs of injection needles inserted therein. The shank portions of the needles also may be curved and not bent so that their internal cannula sections are substantially maintained and fluid flow is not restricted. The injection ends of the needles generally project from the injection needle support in a substantially parallel configuration and in close proximity to each other to allow the substantially simultaneous penetration of the skin of a recipient bird, but with sufficient separation such that the fluids being administered do not substantially mix or interfere with each other once subcutaneously administered.

The injection ends of the needles may also be beveled. In one embodiment of the present invention, the needles are oriented about their longitudinal axes to face the bevels away from each other, thereby directing the two fluid flows exiting from the injection ends into opposite directions. With the present invention, up to four needles may be used to deliver up to four doses of vaccines or drugs. If four needles are used, the needles are oriented about their longitudinal axes to face the bevels away from each other, thereby directing the fluid flows exiting from the injection ends into opposite directions.

In the injection delivery systems of the present invention, the injection needle(s) is/are operably connected via a fluid connection to a metering device. In one embodiment of the present invention, the metering device includes an air cylinder that is used to deliver pressurized air to a plurality of cylindrical metal shafts in order to deliver precise metered doses of drugs or vaccines. In another embodiment of the present invention, the metering device includes a single piston that is used to drive a plurality of plungers of a plurality of vaccine or drug containers, i.e. syringes, in order to dispense multiple metered doses of vaccines or drugs.

In addition to the larger, stationary injection delivery device, another embodiment of the present invention is directed to a hand held injection device that allows a user greater mobility and flexibility when injecting birds.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Additional objects and aspects of the present invention will become more apparent upon review of the detailed description set forth below when taken in conjunction with the accompanying figures, which are briefly described as follows.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that various modifications, combination, additions, deletions and variations can be made in the present invention without departing from the scope or spirit of the invention. For instance, features illustrated or described as part of one embodiment can be used in another embodiment to yield a still further embodiment. It is intended that the present invention covers such modifications, combinations, additions, deletions and variations as come within the scope of the appended claims and their equivalents.

The injection delivery systems according to the present invention are useful to deliver substantially simultaneously multiple fluid doses of a vaccine or a drug composition to a recipient such as, but not limited to, birds whether they are newly hatched birds or older birds. The injection delivery systems of the present invention also allow the co-delivery of vaccines such as herpes virus of turkey (HVT) vaccine with compositions such as antibiotics that may otherwise reduce the therapeutic efficacy of a live virus vaccine. The injection delivery systems of the present invention also provide for a hand held delivery device that can use either multiple needles to deliver multiple doses of a vaccine or drug or can use a single needle that mixes multiple doses of a vaccine or drug at the needle. Additionally, the injection delivery systems of the present invention provide for metering devices that deliver metered doses of a vaccine or drug composition to the injection device. Lastly, with all of the injection delivery systems of the present invention, needle free (needleless) technology may be used to deliver the multiple doses of a vaccine or drug either using multiple delivery routes or a single delivery route.

Figure 1:
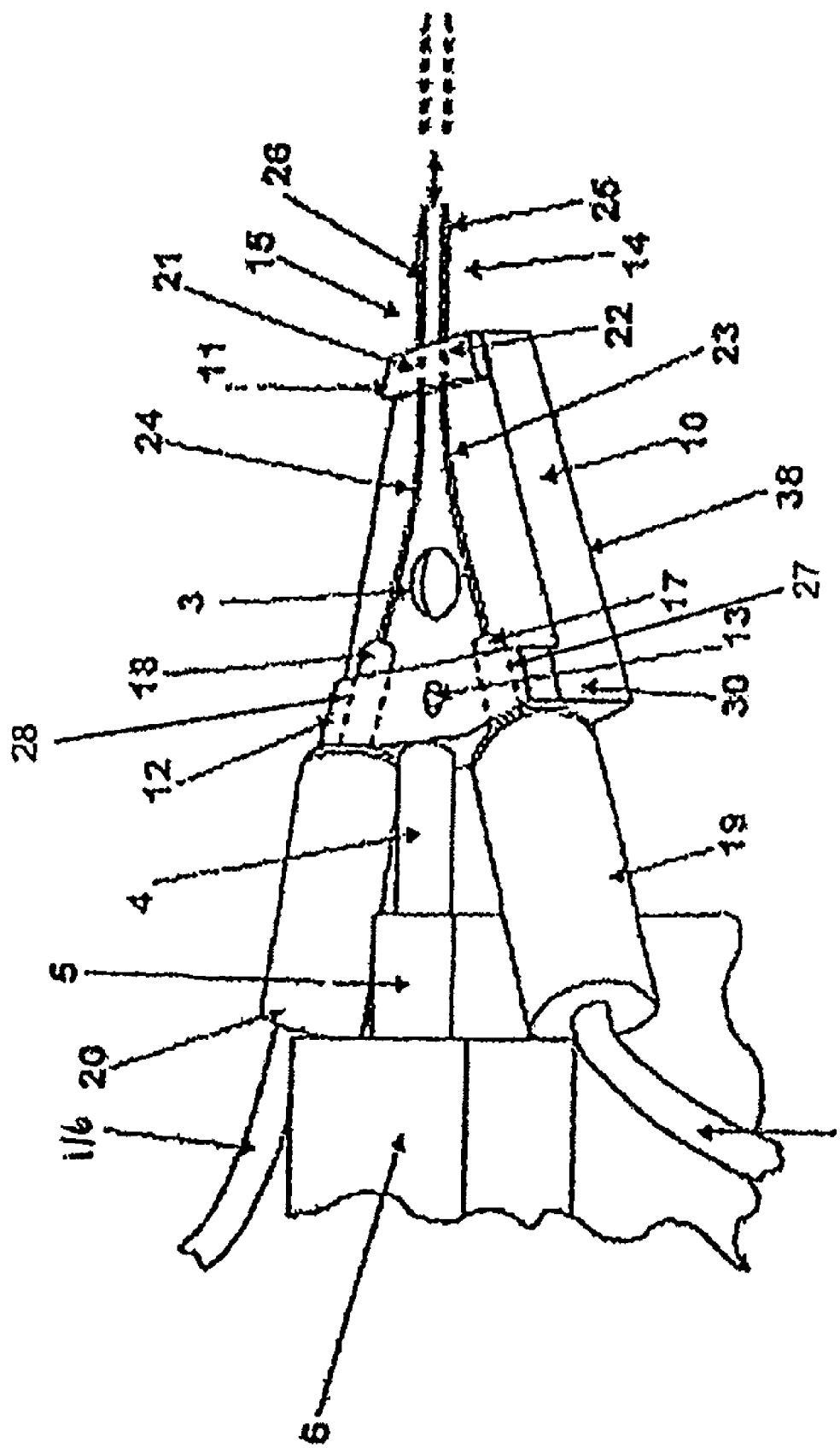
FIG. 1 is a perspective view of a needle assembly of an injection device according to one embodiment of the present invention.

Referring now to FIG. 1, one embodiment of the present invention provides an injection delivery device that includes an injection needle support 10 adapted to receive anywhere from one to four injection needles. As will be apparent to those skilled in the art, if the vaccines or drug compositions to be injected are stable or otherwise compatible when commingled, multiple doses of vaccines or drugs may be injected with the use of a single needle or delivery route. If, however, the vaccines or drug compositions to be injected are not stable or are otherwise incompatible when commingled, multiple doses of vaccines or drugs may be injected using multiple needles or delivery routes. When referring to FIGS. 1 and 2, which provide a nonlimiting example of one embodiment of the present invention, reference will be made to a delivery device that includes two injection needles 14, 15 for delivering vaccines or drugs via two delivery routes.

The injection needle support 10 comprises a base 38 having a base plate 30 and an end plate 11 disposed thereon. The base 38 may be any geometric shape, such as square, rectangular, circular or the like, that will rigidly hold the base plate 30 and the end plate 11 in a fixed spatial relationship. The base 38 may be a solid plate or a frame defining a hole as shown, for example, in FIG. 1. In preferred embodiments, the base 38 is triangular or trapezoidal, with the end of the base 38 having the end plate 11 thereon being narrower than the end having the base plate 30, as shown in FIG. 1. The end plate 11 has two substantially parallel bores 21, 22, each bore capable of receiving a shank 23, 24 of one of the injection needles 14, 15. Suitable injection needles 14, 15 for use in the system of the present invention each generally will comprise a hub or distal end 17, 18 and an injection or proximal end 25, 26 disposed at the opposite end of the shank 23, 24. Preferably, the injection end 25, 26 of each needle is sharpened to ease penetration of the skin of a recipient bird, and further is typically beveled.

The injection needle support 10 of the present invention further comprises recesses 27, 28 in the base plate 30. The recesses 27, 28 are configured to receive the hubs 17, 18 of the injection needles 14, 15 and which may be held in position in the recesses 27, 28 by a releasable or backing plate clamp 12. The clamp 12 will typically be secured with a set screw or similar fastener 13 to prevent the needle hubs 17, 18 from disengaging from the recesses 27, 28. Fluid connections 19, 20 are provided and generally are mounted in communication with the recesses 27, 28 and are also able to engage with the hubs 17, 18 held in the recesses 27, 28, thereby allowing fluids to pass into the injection needles 14, 15 from a fluid supply source (not shown).

The injection needles 14, 15 may be attached to the injection needle support 10 by passing the injection ends 25, 26 of injection needles 14, 15 through a bore 21, 22 and placing a hub 17, 18 in a recess 27, 28 of the base plate 30. The clamp 12 is then positioned on the base plate 30 and secured over the needle hubs to prevent the hubs 17, 18 from being displaced from the recesses 27, 28 and the injection needle support 10. In one embodiment of the present invention, the clamp 12 is a detachable plate. In another embodiment, the clamp 12 can be connected to the injection needle support 10 along a hinge mechanism that allows the clamp to be displaced, but not removed from, the injection needle support 10. Exemplary fasteners for securing the clamp 12 in a closed configuration and which can be easily released to allow the injection needles 14, 15 to be easily replaced when blunted, blocked or otherwise become unsuitable for injecting birds include, but are not limited to, a screw means or opposed polarity magnets, and the like.

The injection needles 14, 15 can be replaced by releasing fasteners 13 of the clamp 12, lifting the hub 17, 18 from the recess 27, 28, disconnecting the needles 14, 15 from fluid connectors 19, 20, and extracting the respective needle 14, 15 from the end plate 11 of the needle support. Substitute injection needles 14, 15 may then be introduced to the injection needle support 10 by reversing this order of operation.

In one embodiment of the present invention, the distance separating the recesses 27, 28 from one another exceeds the distance between the bores 21, 22. In such an embodiment, the injection ends 25, 26 of injection needles 14, 15, once placed into position in the injection needle holder 10, generally will remain substantially parallel while the shanks 23, 24 between the hubs 17, 18 and the end plate 11 are curved. The shanks 23, 24, however, are preferably not bent, so as to maintain unimpeded fluid flows through the cannula of the needles 14, 15. Alternatively, the distance separating the recesses 27, 28 can be about, or substantially the same as, the distance between the bores 21, 22 of the plate 11 so that the needle shanks 23, 24 are substantially parallel.

In the various embodiments of the injection delivery devices of the present invention, the injection ends 25, 26 of the injection needles 14, 15, when inserted into the injection needle support 10, will project beyond the end plate 11. The extent to which the injection ends 25, 26 project beyond the end plate 11 may be selected manually or automatically according to the type or size of the recipient birds. The selected length of the injection ends 25, 26 of the needles and the degree of the extension movement of the carrier 4 imparted by the actuator 6 also determines whether the injection of fluid(s) into the recipient bird is subcutaneous or intramuscularly by affecting the depth of penetration of the needles. Injection needles 14, 15 suitable for use in the present invention may be from 2-20 gauge. Preferably, the injection ends 25, 26 are sharpened and beveled. For example, beveled injection ends 25, 26 orientated in substantially opposite directions are shown in FIG. 1. If more than two injection needles are used, the beveled injection ends of all of the needles can be oriented in substantially opposite directions. This substantially opposed orientation of beveled injection ends 25, 26 can direct injected fluids in divergent directions to reduce potential co-mingling of incompatible fluids within the tissues of the recipient bird.

Figure 2:
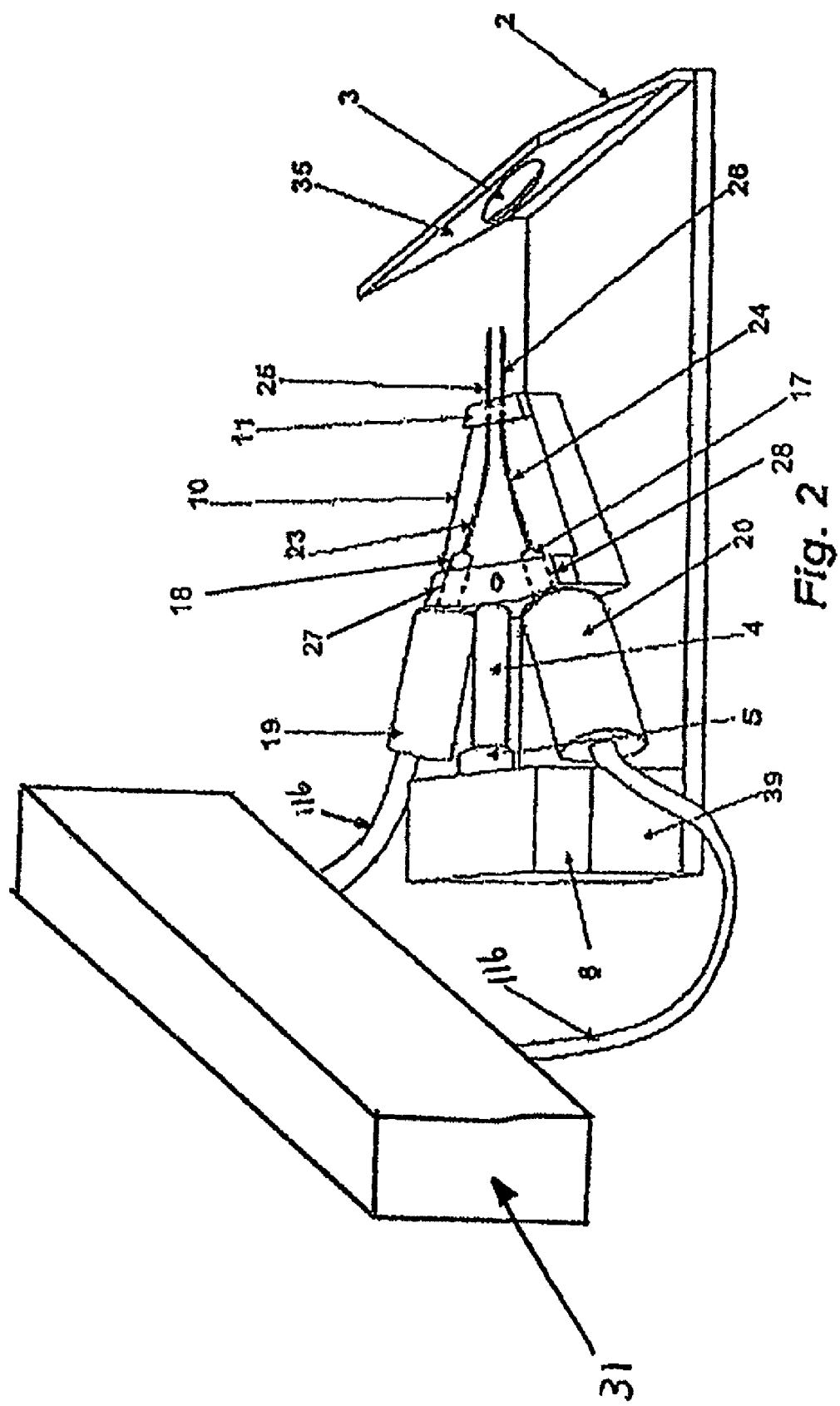
FIG. 2 is a schematic view of the injection delivery system according to one embodiment of the present invention.
Figure 3:
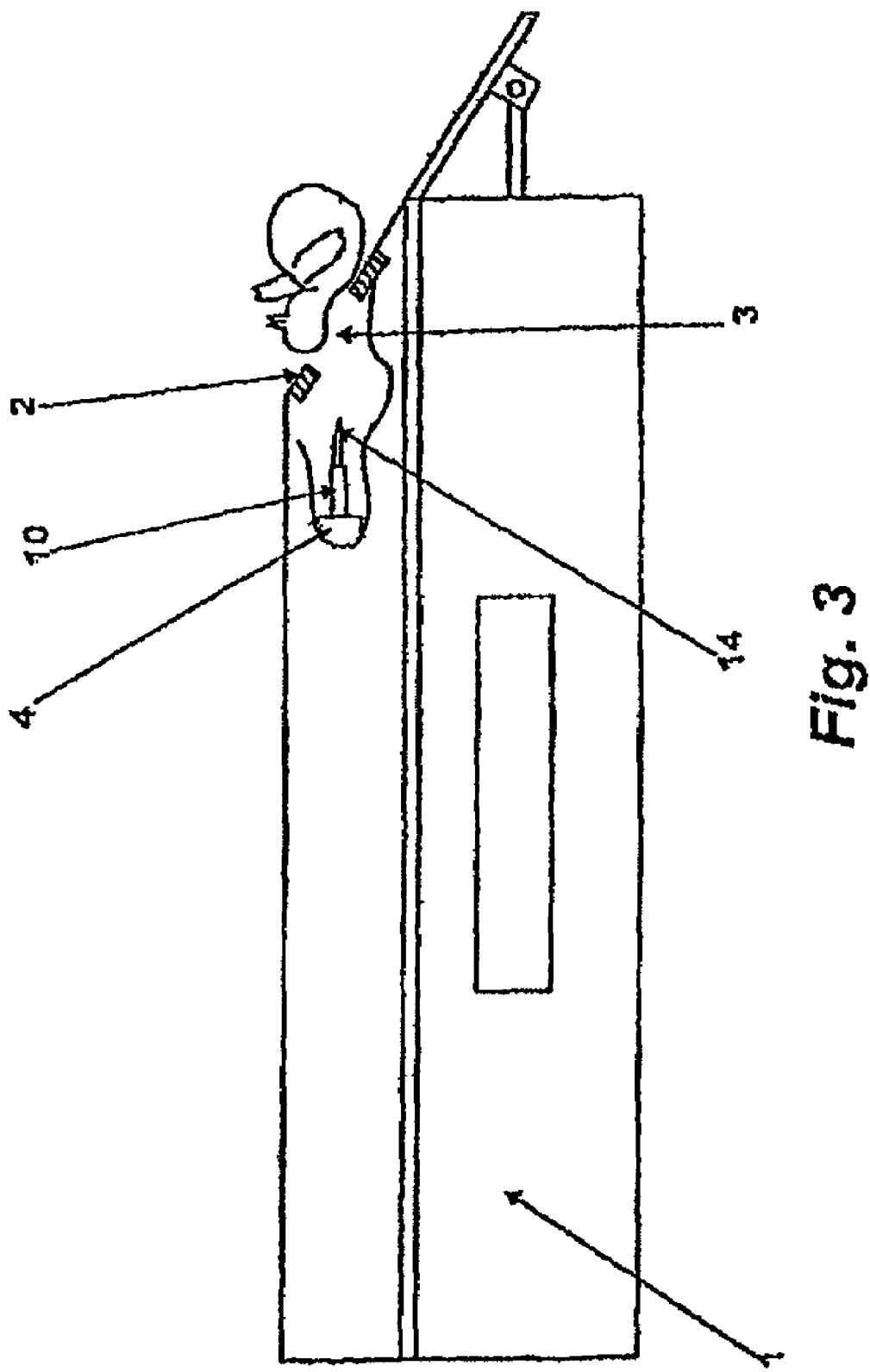
FIG. 3 is a schematic view of the injection delivery system according to one embodiment of the present invention.

As illustrated in FIGS. 2 and 3, the present invention provides an injection needle support 10 connected to a carrier 4 slidably disposed in a guide 5. The carrier 4 is operably connected to an actuator 6 configured to reciprocally move the carrier 4 and injection needle support 10 from a retracted position to an extended injection position. Suitable actuators 6 include, but are not limited to, a solenoid, electric motor or driver, or a hydraulic actuator, where the selected actuator 6 further comprises a power source. The actuator 6 is also operably connected to a switch 35 that may include, but is not limited to, a manually activated switch, or an automatic switch such as a pressure switch or sensor, or a photoelectric switch. It is contemplated that the switch will be reversible so that in a first position the carrier 4 and injection needle support 10 are extended by the actuator 6 and, in a second position, the carrier 4 and the injection needle support 10 may be retracted away from the injected recipient bird. It is further contemplated that the carrier 4 and the injection needle support 10 may be automatically retracted by, for example, a spring-biased device once the actuator 6 is deactivated.

Figure 4:
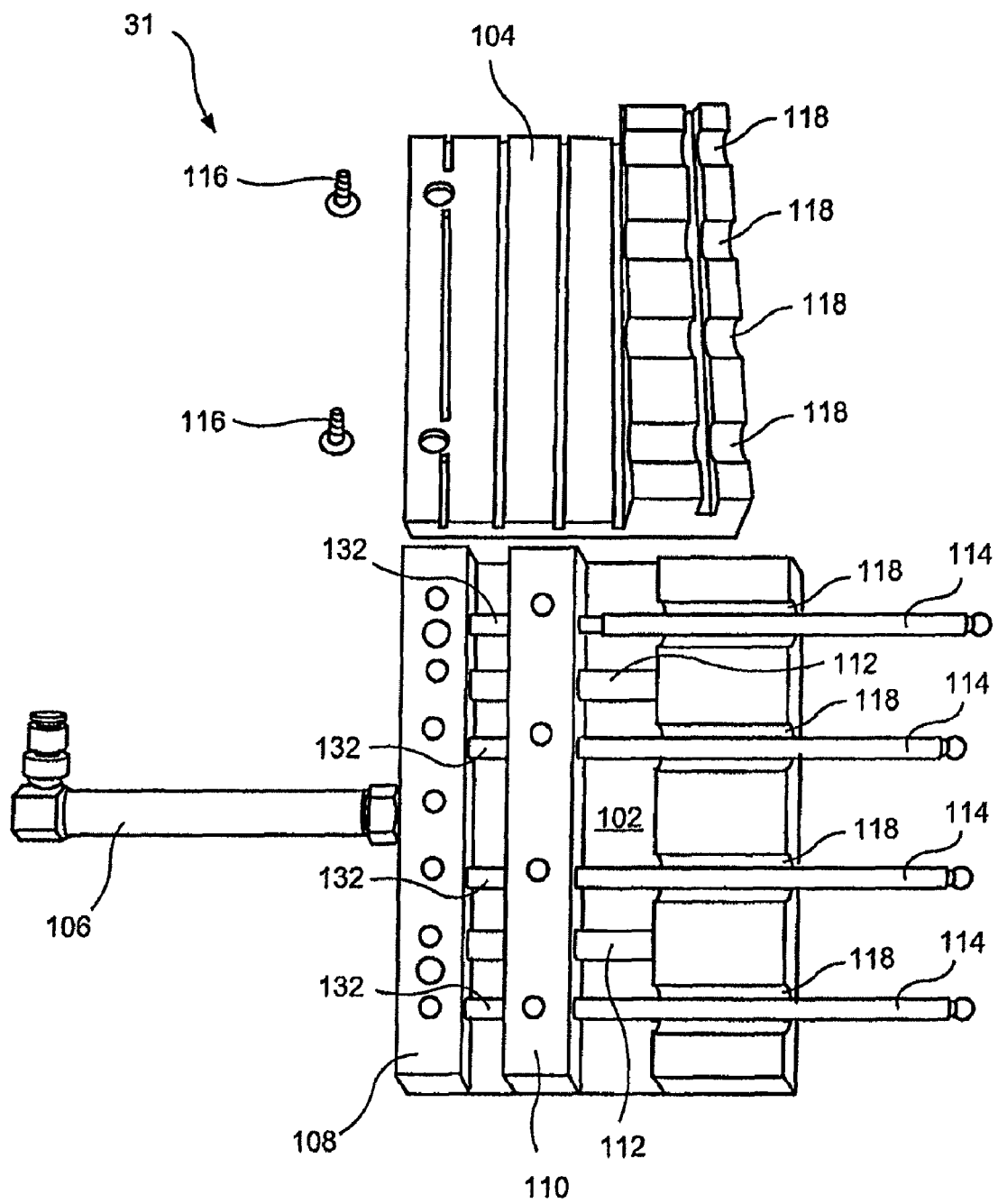
FIG. 4 is a perspective view of a top portion and a bottom portion of a metering device according to one embodiment of the present invention.
Figure 5:
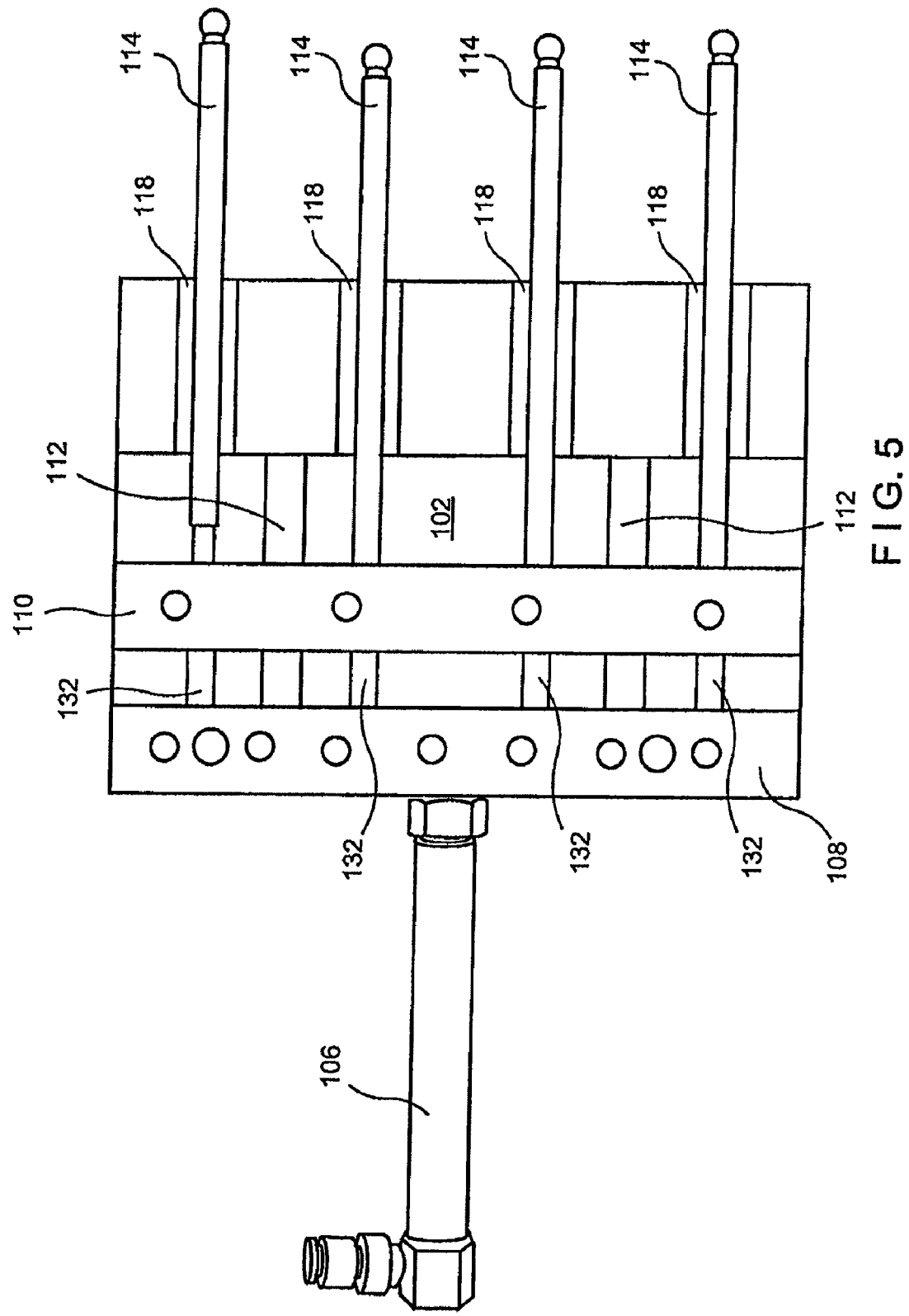
FIG. 5 is a plan view of a bottom portion of a metering device according to one embodiment of the present invention.

As depicted in FIG. 2, the injection delivery systems of the present invention further comprise a metering device 31. Depicted in FIGS. 4 and 5 is a metering device according to one embodiment of the instant invention. As shown in the figures, the instant metering device comprises a base or bottom portion 102, a top portion 104, an air cylinder 106, a manifold 108, a drive bar 110, a pair of guide shafts 112 and a plurality of elongated cylindrical shafts 114 that may be constructed out of metal or a similar material. The top portion 104 attaches to the base or bottom portion 102 by way of a plurality of screws 116. As can be seen in the figures, both the base 102 and top portion 104 have a plurality of grooves 118 to receive the plurality of elongated cylindrical shafts 114.

Figure 6:
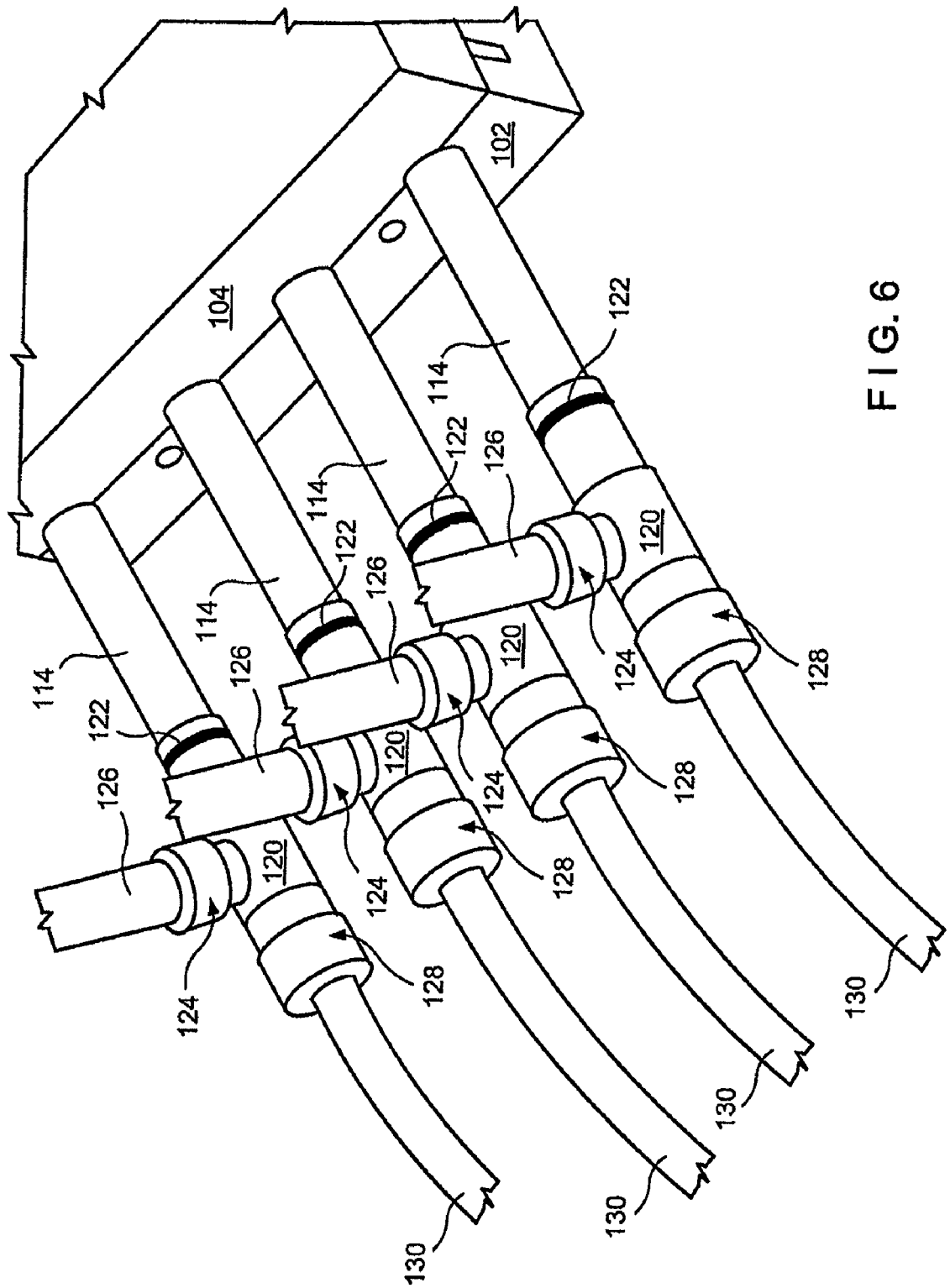
FIG. 6 is a perspective view of the fluid connections of a metering device according to one embodiment of the present invention
Figure 7:
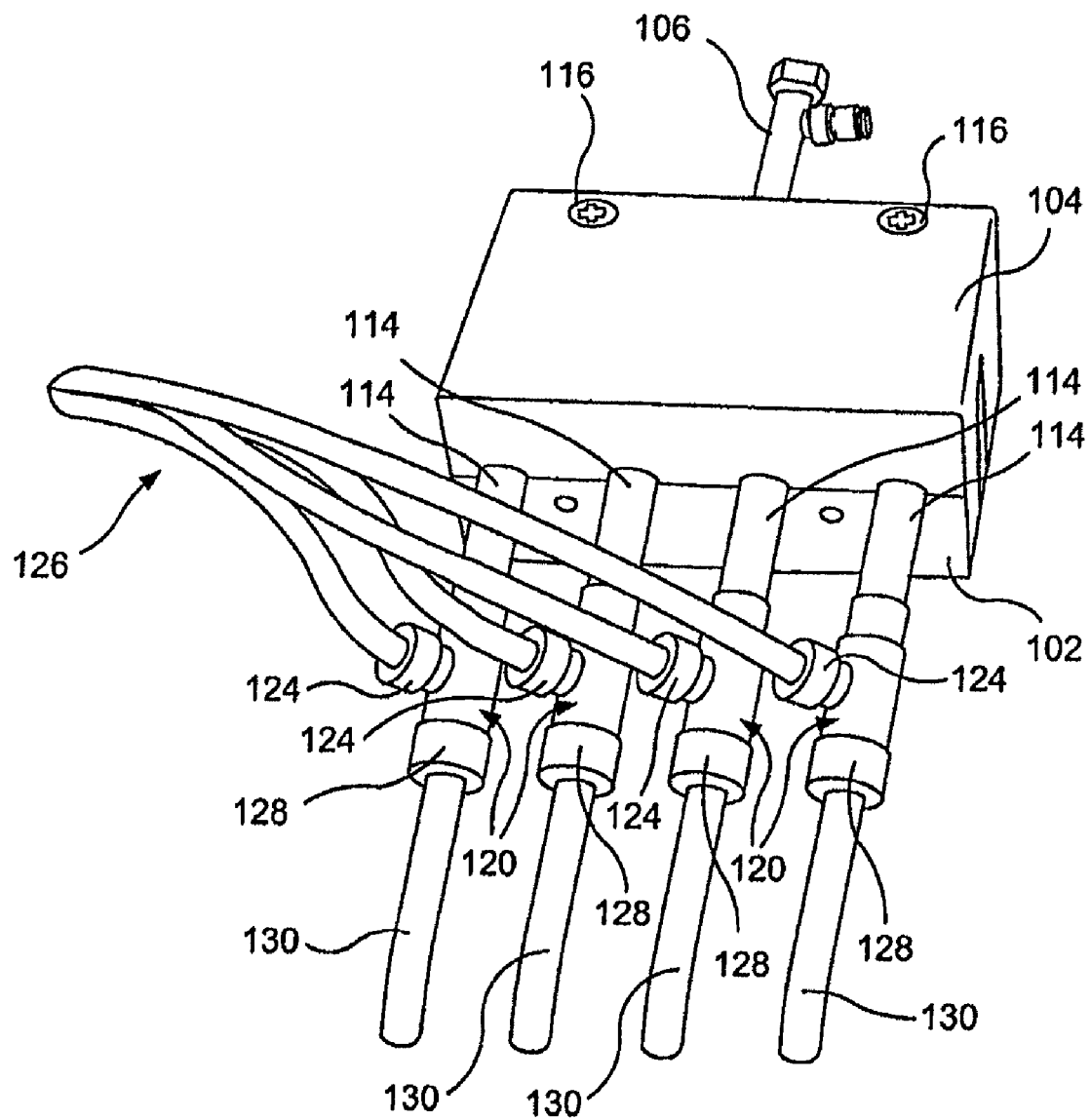
FIG. 7 is a perspective view of the partially assembled metering device depicted in FIGS. 4 and 5 fully assembled according to one embodiment of the present invention.

The metering device of the instant embodiment further comprises a plurality of check valves 120. As depicted in FIG. 6, the check valves 120 attach to the ends of the elongated cylindrical shafts 114. To keep the check valves 120 firmly attached to the metal shafts 114, they are heat welded to the ends of the cylindrical shafts 114. The check valves 120 comprise an O-ring gasket 122, an inlet port 124 that allows fluid communication to a drug or vaccine supply by way of tubing 126 and a outlet port 128 that attaches to fluid supply lines 130 that deliver the metered dose of a drug or vaccine to the injection delivery device. FIG. 7 depicts an assembled metering device according to the instant embodiment.

Operation of the metering device according to the instant embodiment is as follows. Pressurized air is delivered to the manifold 108 by way of the air cylinder 106. The manifold 108 distributes the pressurized air to a plurality of cylinders 132. The pressurized air causes the plurality of cylinders 132 to move the drive bar 110 in a direction away from the manifold 108 or to the right in the figures. The drive bar 110 rides on the guide shafts 112 thereby remaining substantially parallel to the manifold 108 as it moves along the guide shafts 112. Movement of the drive bar 110 away from the manifold 108 causes the plurality of cylindrical metal shafts 114 to also move in a direction away from the manifold 108. Movement of the cylindrical shafts 114 in a direction away from the manifold 108 results in metered doses of a drug or vaccine being expelled from the check valves 120 and delivered to the injection delivery device by way of the fluid supply lines 130. If, as previously discussed, the vaccines or drug compositions to be injected are stable or otherwise compatible when commingled, the fluid supply lines 130 can be attached to a single injection device, i.e. needle, so that the vaccines or drugs can be injected using a single injection device or route. If, however, the vaccines or drug compositions to be injected are not stable or otherwise incompatible when commingled, the multiple individual fluid supply lines 130 can each connect to a separate delivery device so that the vaccines or drugs can be injected separately via multiple delivery routes.

The dosage amount is determined by the diameter of each cylindrical shaft 114. Therefore, for smaller doses, for example 0.3 ml., a smaller diameter cylindrical shaft 114 will be used. For a larger dose of a vaccine or drug, for example 0.5 ml., a larger diameter cylindrical shaft 114 will be used. Therefore, varying doses of multiple drugs or vaccines can be delivered using a single metering device by using cylindrical shafts 114 having different diameters.

Figure 8:
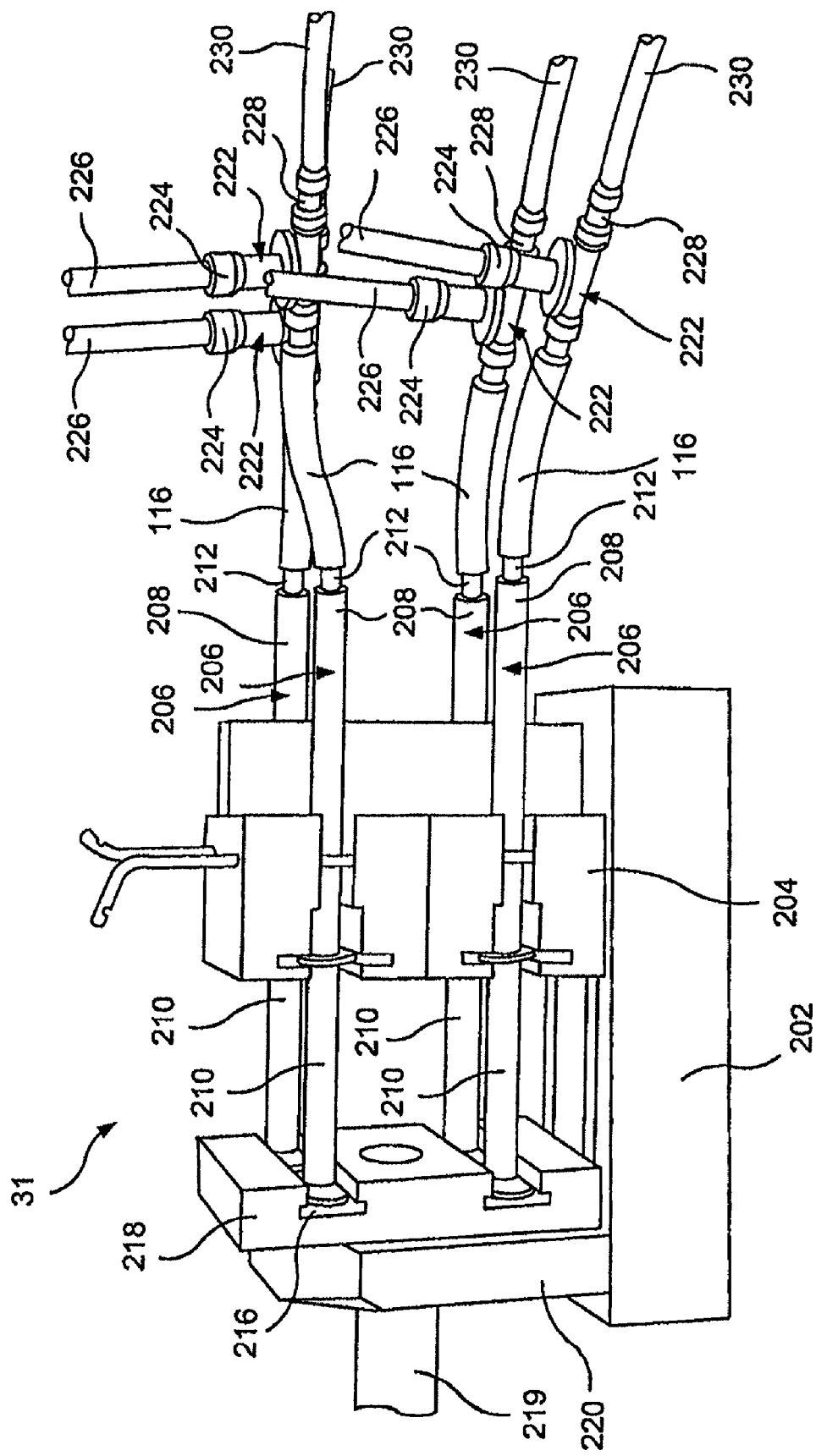
FIG. 8 is a side plan view of a metering device according to one embodiment of the present invention.

In another embodiment of a metering device according to the instant invention, as depicted in FIG. 8, instead of using a plurality of cylindrical metal shafts to deliver metered doses of a drug composition or vaccine, a plurality of syringes may be used. As depicted in the FIG. 8, the metering device 31 includes a platform 202 that includes a holding or clamping means 204 that can simultaneously hold up to 4 separate vaccine or drug containers 206. As depicted in the figure, in the instant embodiment, the containers 206 are syringes. The syringes comprise a body portion 208, a moveable plunger portion 210 and a drug dispensing portion 212 that attach to fluid lines 116.

A clamping pressure is applied to the body portion 208 of the syringes 206 by a plurality of threaded clamping rods 214, thereby clamping the containers 206 in a fixed position. The moveable plunger portions 210 of the syringes 206 slidably engage slots 216 in a moveable plate 218 so that the plunger portions 210 slide in and out as the moveable plate 218 moves back and forth in a direction parallel to the movement of the plunger portions 210. A piston 219 is disposed through and supported by an aperture in a support block 220 and attaches to the moveable plate 218 such that the piston 219 and the moveable plate 218 slide back and forth as a unitary structure. Consequently, as the piston 219 and the moveable plate 218 slide to the right in the figure, movement of the plunger portions 210 in a corresponding direction results in multiple doses of drugs or vaccines being dispensed through the dispensing portions 212 of the syringes 206.

In addition, the instant metering device 31 also includes a plurality of check valves 222. As depicted in FIG. 8, the check valves 222 attach to the fluid lines 116. The check valves 222 an inlet port 224 that allows fluid communication to a drug or vaccine supply by way of tubing 226 and a outlet port 228 that attaches to fluid supply lines 230 that deliver the metered dose of a drug or vaccine to the injection delivery device.

Because the piston 219 moves all of the plunger portions 210 of the syringes 206 the same distance, if different doses of vaccines or drugs are desired, the diameters of the body portion 208 of the syringes must be sized so that the correct doses are delivered by movement of the piston 219.

Similarly, as previously discussed for the preceding embodiment, if the vaccines or drug compositions to be injected are stable or otherwise compatible when commingled, the multiple individual fluid lines 116 can be attached to a single injection device, i.e. needle, so that the vaccines or drugs can be injected using a single injection device or route. If, however, the vaccines or drug compositions to be injected are not stable or otherwise incompatible when commingled, the multiple individual fluid lines 116 can each connect to a separate delivery device so that the vaccines or drug compositions can be injected separately via multiple delivery devices and routes.

Figure 9:
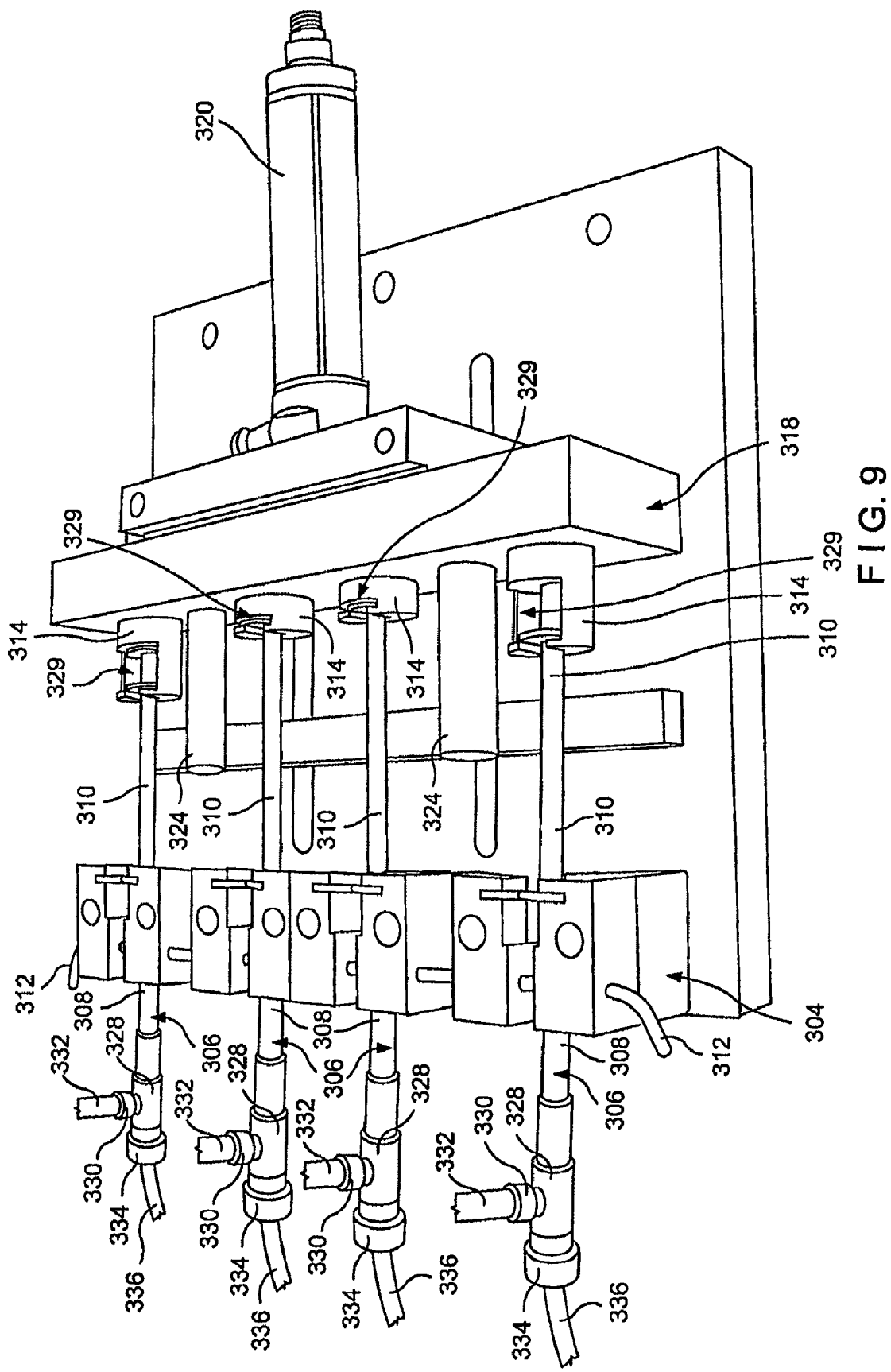
FIG. 9 is a perspective view of a metering device according to one embodiment of the present invention.

Another embodiment of a metering device according to the instant invention is depicted in FIG. 9. Similar to the previous embodiment, instead of using a plurality of cylindrical metal shafts to deliver metered doses of a drug or vaccine, a plurality of syringes may be used. As depicted in FIG. 9, the metering device 31 includes a platform 302 that comprises a holding or clamping means 304 that can simultaneously hold up to 4 separate syringes 306, which may contain different drug compositions or vaccines. The syringes 306 comprise a body portion 308, a moveable plunger portion 310 and a drug dispensing portion (not shown in the figure) that attach to fluid lines (not shown in the figure). A clamping pressure is applied to the body portion 308 of the syringes 306 by a plurality of threaded clamping rods 312, thereby clamping the syringes 306 in a fixed position. The moveable plunger portions 310 of the syringes 306 are seated in carrier devices 314. The carrier devices 314 are attached to a moveable plate 318 so that the plunger portions 310 slide in and out as the moveable plate 318 moves back and forth in a direction parallel to the movement of the plunger portions 310.

The metering device 31 also includes an air cylinder 320 which is designed to receive pressurized air. Within the air cylinder 320 is disposed a piston. The piston is disposed through and is supported by an aperture in a support block 322 and attaches to the moveable plate 318 such that the piston and the moveable plate 318 slide back and forth as a unitary structure as compressed air enters the air cylinder 320. Consequently, as the piston and the moveable plate 318 slide to the left in the figure, movement of the plunger portions 310 in a corresponding direction results in multiple doses of drugs or vaccines being dispensed through the dispensing portions of the syringes 316. As can further be seen in the figure, the metering device also includes a pair of guide shafts 324 that attach to a stationary bar 326 and upon which the moveable plate 318 slidably moves or rides. The guide shafts 324 limit movement of the moveable plate 318 to a direction substantially perpendicular to the support block 322.

In addition, the instant metering device 31 also includes a plurality of check valves 328. As depicted in FIG. 9, the check valves 328 attach to the fluid lines 336. The check valves 328 have an inlet port 330 that allows fluid communication to a drug or vaccine supply by way of tubing 332 and a outlet port 334 that attaches to fluid supply lines 336 that deliver the metered dose of a drug or vaccine to the injection delivery device.

As can be seen in FIG. 9, the length of the two interior carrier devices is shorter than the length of the two exterior carrier devices. As can also be seen in FIG. 9, each carrier device has an internal cavity 329 in which the top end of the moveable plunger portion 310 of the syringe 306 is placed. The length of this internal cavity 329 and, hence the length of the carrier device 314, determines the dose of the vaccine or drug to be delivered to the injection device. A longer carrier device 314 with a longer internal cavity 329 permits the moveable plate 318 to move the carrier device 314 a longer distance before the back wall of the carrier device 314 engages the top end of the moveable plunger portion 310 of the syringe 306, resulting in the moveable plunger portion 310 being depressed within the body portion 308 of the syringe 306, thereby delivering the desired dose of a drug or vaccine to the injection delivery device. Accordingly, a shorter carrier device 314 delivers a higher dose of a drug or vaccine to the injection delivery device than a longer carrier device 314.

As previously discussed for the preceding embodiment, if the vaccines or drug compositions to be injected are stable or otherwise compatible when commingled, the multiple individual fluid lines can be attached to a single injection device, i.e. needle, so that the vaccines or drugs can be injected using a single injection device or route. If, however, the vaccines or drug compositions to be injected are not stable or otherwise incompatible when commingled, the multiple individual fluid lines can each connect to a separate delivery device so that the vaccines or drug compositions can be injected separately via multiple delivery devices and routes.

In addition to comprising an injection delivery device and a metering device, the injection delivery systems according to the instant invention further generally includes a control means and power source to activate the metering device 31 to deliver a plurality fluid doses to a bird maintained against the retaining plate 2, and cause movement of the needle support to its operative injection position.

Additionally, as depicted in FIG. 3, the needle injection device of the present invention also generally includes a retaining plate 2 having an aperture 3 therein. The retaining plate 2 and the aperture 3 are positioned so that when the carrier 4 and the injection needle support 10 are in an extended position, the injection ends 25, 26 project through and beyond the aperture 3 to a selected distance that allows injection of a fluid dose into a recipient bird. The chick or other small bird can be slightly pressed against the retaining plate 2 by the operator or otherwise restrained in a desired position for injection. The retention means also may be sloped with regard to the travel axis of the needles.

In operation of the injection delivery systems of the present invention, a chick or other small bird is maintained against the retaining plate 2 with the area of the bird to receive the fluid dose(s) positioned over the aperture 3 in the retaining plate 2. Generally, the neck of the bird is the targeted area, but any other areas of the bird, including the breast, thigh, wing, leg, neck and the like may be selected to receive the delivered fluid dose. An optional restraint may be used to prevent escape of the bird. Pressure of the bird against the retaining plate 2 can engage and actuate a switch to activate the actuator 6 to move the carrier 4 and the injection needle support 10 attached thereto, to a predetermined extended operative injection position. The injection ends 25, 26 of the needles 14, 15 project through the retaining plate 2 and the aperture 3 therein, to penetrate the skin overlying the selected injection point of the bird.

When the carrier 10 and the needles 14, 15 thereon are in the extended position with the injection 25, 26 ends, in the bird, the metering device 31 is actuated by a switch means activated automatically, as described in U.S. Pat. No. 5,312,353, or by a system operator to deliver the fluid doses through their respective needles 14, 15. The volumes for the delivered doses are selected depending on the treatment protocol administered to the birds and are selected using the computer unit of the metering device. The volumes can be identical or different between needles. It is contemplated to be within the scope of the present invention for the fluid doses delivered to a recipient bird to be the same therapeutic fluids or different. The delivery systems of the present invention can deliver the same fluid to at least two different positions in the bird or at least two different fluids that may be incompatible or unstable when mixed.

Figure 10:
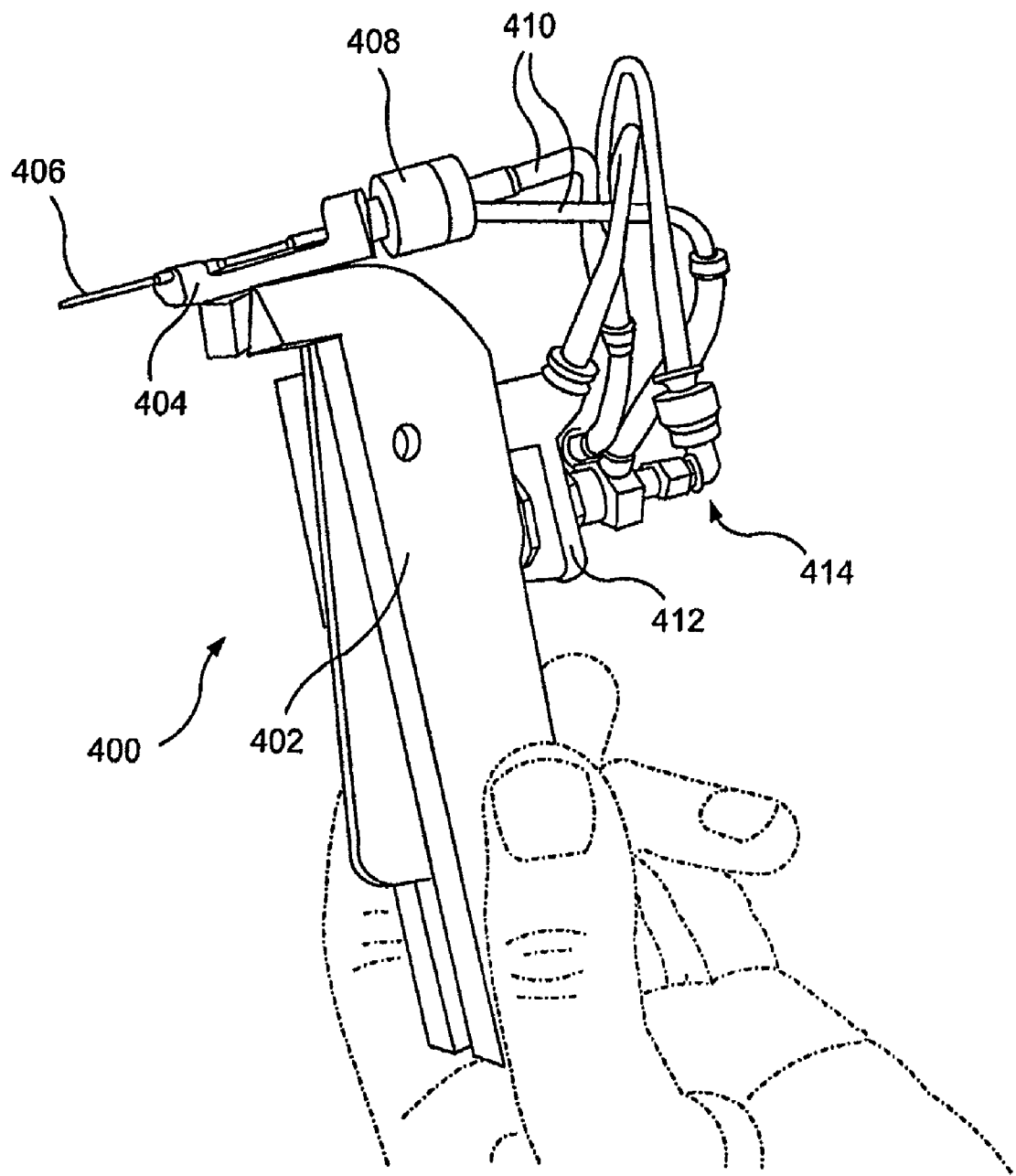
FIG. 10 is a perspective view of a needle assembly of an injection device according to one embodiment of the present invention.

In addition to the previously disclosed injection delivery device, a smaller, hand held injection device 400, depicted in FIG. 10, may be used to inject multiple doses of a drug or vaccine. The hand held device 400 includes a base 402, which can be used as a handle and upon which all of the components of the hand held device 400 are mounted. The hand held device 400 further includes a needle support 404 and at least one needle 406. As can further be seen in FIG. 10, the needle 406 is mounted on the needle support 404 such that it is substantially perpendicular to the base 402.

Attached to the needle 406 is a fluid connection 408. As can be seen in FIG. 10, the fluid connection 408 allows one or multiple fluid lines 410 to be connected to the needle 406. In the instant embodiment, as depicted in FIG. 10, the fluid connection 408 permits two fluid lines 410 to be connected to a single needle 406 in order to allow two compatible vaccines or drugs to be delivered using a single needle or delivery route. If the vaccines or drugs are incompatible, a separate fluid connection 408 is used to connect each fluid line 410 to a separate needle 406. In order to keep the fluid lines 410 from pulling away from the fluid connections 408, the fluid lines 410 attach to the base 402 by way of a mounting bracket 412 and a series of additional fluid connectors 414.

Similar to the larger injection delivery device previously disclosed, if the vaccines or drug compositions to be injected are stable or otherwise compatible when commingled, multiple doses of vaccines or drugs may be injected with the use of a single needle or delivery route. If, however, the vaccines or drug compositions to be injected are not stable or are otherwise incompatible when commingled, multiple doses of vaccines or drugs may be injected using up to four needles to deliver four separate doses of a vaccine or drug. In this case, up to four needles may be mounted on the needle support 404.

In contrast to the previously disclosed larger injection systems, the instant hand held injection device allows a user more mobility and greater flexibility when injecting birds.

In addition to using needles to deliver the metered doses of vaccines or drug compositions, as previously disclosed, needleless technology may be used with all of the disclosed injection delivery devices to delivery the metered doses of vaccines and drug compositions.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An injection delivery system comprising:
   (a) a hand held injection needle device; and
   (b) a metering device comprising:
   (1) an air cylinder comprising a piston, wherein the air cylinder is designed to receive pressurized air;
   (2) a plurality of fluid containers;
   (3) a moveable plate coupled to the piston such that the moveable plate and the piston move as a unitary structure as the pressurized air enters the air cylinder;
   (4) a plurality of carrier devices;
   (5) a support block configured to support at least a portion of the piston; and
   (6) a plurality of guide shafts wherein the injection delivery device further comprises an injection needle support, comprising:
   (7) a base;
   (8) an end plate having at least two substantially parallel bores, wherein each bore is suitable for receiving a shank portion of at least one injection needle;
   (9) a base plate having at least two recesses, each recess configured for receiving a hub of the at least one injection needle;
   (10) at least two fluid connections, each fluid connection capable of communicating with the injection needle hub received by one of the recesses of the base plate.

* * * * *